United States Patent [19]

Fox et al.

[11] Patent Number: 5,373,085
[45] Date of Patent: Dec. 13, 1994

[54] MEMORY ENHANCING THERMAL PROTEINS

[76] Inventors: Sidney W. Fox, 707 S. Valley Rd., Carbondale, Ill. 62901; James F. Flood, 322 E. Lockwood, Webster Groves, Mo. 63119

[21] Appl. No.: 951,788

[22] Filed: Sep. 28, 1992

[51] Int. Cl.$^5$ .................................. C08G 69/10
[52] U.S. Cl. ........................ 528/328; 528/331
[58] Field of Search ............... 528/363, 328, 331; 530/300; 514/2

[56] References Cited

U.S. PATENT DOCUMENTS 4,996,292  2/1991  Fox et al. ..................... 528/331
5,089,545  2/1992  Pol ............................... 524/17

Primary Examiner—John Kight, III
Assistant Examiner—Jeffrey Culpeper Mullis
Attorney, Agent, or Firm—Peter R. Bahn

[57] ABSTRACT

Memory enhancing thermal proteins were synthesized from heating aspartic acid, glutamic acid, proline and tryptophan above 100° C. Two hydrophobic and one non-hydrophobic polymer were injected intracerebroventricularly into the brains of mice after the mice had undergone partial training in footshock avoidance conducted in a T-maze. When retention of footshock avoidance was tested one week later, the hydrophobic polymers enhanced retention while the non-hydrophobic polymer did not.

2 Claims, No Drawings

MEMORY ENHANCING THERMAL PROTEINS

FIELD OF THE INVENTION

This invention is related to the fields of protein engineering and pharmacology in general, and to the fields of thermal protein engineering and psychopharmacology in particular.

BACKGROUND OF THE INVENTION

We have found that thermal analogs of proteins, or thermal proteins, can be synthesized by simply heating α-amino acids (U.S. Pat. Nos. 3,052,655 and 3,076,790). Such thermal polymers have found utility in the microencapsulation of an antitumor agent (U.S. Pat. No. 4,963,364), as an artificial skin (U.S. Pat. No. 4,996,292) in the production of photographic film (U.S. Pat. No. 4,315,072), and in a photovoltaic device (U.S. Pat. No. 4,514,584).

In addition, Sikes and Wheeler found thermal proteins to possess utility as inorganic ion chelators (U.S. Pat. No. 4,534,881). Also, Steiner and Rosen found thermal proteins to have utility for the microencapsulation of numerous types of pharmaceuticals (U.S. Pat. Nos. 4,925,673 and 4,976,968).

Recently, some thermal proteins were found to have neurotrophic properties on cultured fetal rat forebrain neurons (Hefti et al, 1991). Such thermal proteins stimulated neural outgrowth and increased contact with other neurons, as well as prolonging the survival of neural cells. Altered synaptic connections within neural networks has been a basic underlying assumption of the mechanism by which the long term storage of information in the central nervous system occurs (Hebb, 1949). As some thermal proteins were found to promote the formation of synaptic connections within neural networks, it was hypothesized that such thermal proteins might enhance memory processing.

A number of chemical compounds exist which have been shown to improve memory when administered to mice and/or human subjects. Such compounds include nicotine, caffeine, amphetamine, strychnine, picrotoxin, corticosterone, ACTH, hydergine (Flood et al, 1985), and fluoxetine (Flood and Cherkin, 1987).

Memory enhancing compounds can be defined as compounds that: show a relationship between dose and degree of memory improvement; have a time-dependent action such that the longer the compound is administered after training the less effectively it improves memory; act as anti-amnestics; improve memory in more than one task; improve retention when administered before training, at a lower dose than when administered after training; improve retention when administered just prior to a retention test; and improve retention when administered centrally.

As numerous proteins and peptides are known to have various neurological effects, the object of this invention is the synthesis and identification of thermal proteins which have the neurological effect of improving memory processing.

SHORT SUMMARY OF THE INVENTION

Thermal proteins that function as memory enhancers were prepared by heating mixtures of α-amino acids for several hours above 100° C. The compounds were administered to the central nervous system of mice. Mice treated in such fashion were found to retain T-maze footshock avoidance training more efficiently than those not treated. Those thermal proteins found to be most effective were hydrophobic and contained residues of tryptophan.

DETAILED DESCRIPTION OF THE INVENTION

Synthesis of Thermal Proteins

Thermal proteins were produced by heating mixtures of α-amino acids including at least a few percent of aspartic or glutamic acid or both (Fox and Harada, 1966; Fox and Waehneldt, 1986) under hypohydrous conditions. Thermal protein GV-II-100UN was prepared by heating 6.7 g aspartic acid, 7.4 g glutamic acid, 17.3 g proline, and 30.6 g tryptophan (Molar ratios 1:1:3:3 of L forms) for 5.5 hr at 175°–180° C. internal temperature (205° C. in oil bath) under nitrogen. After cooling, free amino acids were removed from the product by mixing it with 200 ml of water and filtering the mixture through Whatman no. 1 paper. The undissolved fraction was dried in a dessicator. Thermal protein RS-III-54 was prepared in a similar manner with 6.7 g aspartic acid, 22.1 g glutamic acid, 10.2 g tryptophan, and 7.9 g cysteine HCl (molar ratios 1:3:1:1). A thermal protein devoid of hydrophobic amino acids, RS-IV-132DD, was formed from 133 g aspartic acid and 147 g glutamic acid (molar ratio 1:1) which was heated at 200° C. internal temperature for 3 hr. To remove the free aspartic and glutamic acis, the product was mixed with 800 ml of water and dialyzed for 24 hr in 1200 ml of water in a membrane with a molecular weight cutoff of 3500 Daltons.

Subjects

CD-1 male mice, six weeks of age, were obtained from Charles River Breeding Laboratories, Wilmington, Mass. Mice were individually caged 24–48 hr prior to training and remained singly housed until retention was tested one week later. Animal rooms were on 12 hr light-dark cycle with lights on at 0600. The mice were trained and tested between 0800 and 1400. Mice were assigned randomly to groups of 15.

Surgery

Mice were prepared for receiving an intracerebroventricular (ICV) injection 24–48 hours prior to training (Flood et al, 1990). In brief, mice were anesthetized with methoxyflurane, placed in a stereotaxic instrument and a hole drilled over the lateral ventricle of the brain where it joins the third ventricle (−0.5 mm relative to bregma, 0.5 right of the central suture). Immediately after training, mice were again placed in the stereotaxic intrument under enflurane anasthesia. Within three minutes after training, a 2 μl solution of polymer or saline was injected over 60 seconds through a 31 gauge needle into the ventricle (1.6 mm deep). This method of injection results in reliable ICV administration. The reliability of the injections was determined by injecting dye in the ventricle; less than 1% failed to show dye in the ventricles.

Training

The T-maze apparatus has been previously described (Flood et al, 1990). It consisted of a black plastic start alley in the shape of a T with a start box at one end and two goal boxes at the other. The floor consisted of stainless steel rods. The start box was separated from the start alley by a plastic guillotine door which prevented the mouse from moving down the alley until the training started.

A training trial started when a mouse was placed into the start box. The guillotine door was raised and a buzzer (55 dB) sounded simultaneously, then 5 sec later a scrambled footshock (0.30 ma) was applied. The goal box that the mouse first entered on this trial was designated as "incorrect" and the footshock was continued until the mouse entered the other goal box, which on all subsequent trials was designated "correct" for that particular mouse. Entry into the correct goal box terminated the buzzer and footshock. At the end of each trial, the mouse was removed from the goal box and returned to its home cage. A new trial began after 30 sec. All mice received four training trials. By using only four training trials, control group retention would be poor and we could determine if thermal proteins improved retention.

Administration of Thermal Proteins

Thermal proteins GV-II-100UN and RS-III-54 were dissolved in 0.1 N NaOH and neutralized with 0.1 N HCl and then diluted with distilled water to the desired concentration. Thermal protein RS-IV-132DD was soluble in saline. All solutions were prepared fresh daily. All three compounds were administered in 2.25, 4.5, and 9.0 μg/brain in 2 μl delivered ICV. Compound RS-III-54 was tested at 1.13 μg/brain as this polymer was particularly effective at enhancing memory retention. The control group received saline ICV. All solutions were coded to prevent experimenter bias.

Test Retention

The retention was tested one week after training by continuing the training until each mouse reaced a criterion of five avoidances in six consecutive training trials. Trials to the first avoidance response and to criterion were used as measures of retention. The results were expressed as the mean and standard error of the mean. The overall significance of the thermal protein treatments on retention was determined by independent one-way analysis of variance (ANOVA) run each measure of retention. Dunnett's t-test was used to make multiple comparisons between each treatment group and the control group (Keppel, 1973).

Analyses of the Polymers

For each analysis, 15 mg of polymer was hydrolyzed in 300 ml of 4 N methansulfonic acid at 100° C. for 20 hr. Each solution was evaporated and the nanomoles of a representative sample were determined on a Jeolco Amino Acid Analyzer. The molar ratios for each polymer were given above and the analyses of the hydrolyzates is given in Table 1.

Memory Retention

Thermal proteins GV-II-100UN and RS-III-54, but not RS-IV-132DD, improved retention in a dose-dependent manner by either measure of retention. Three separate one-way ANOVA's run on either trials to first avoidance response or trials to the five avoidance criterion indicated that the thermal proteins had significant experimental effects (Table 2). Thermal protein RS-IV-132DD didn't effect performance on the retention test ($F<1$). A subsequent analysis of the differences between means of the control (0 μg) and the groups receiving polymer by Dunnett's t-test indicated a dose-dependent reduction in the mean trials to first avoidance or to reach the five avoidance criterion (Table 2).

TABLE 1

| AMINO ACIDS ASSAYED IN HYDROLYZATES (nmoles) | | | |
|---|---|---|---|
| Amino Acid* | GV-II-100UN | RS-III-54 | RS-IV-132DD |
| Alanine | 2 | 24 | <0.5 |
| Aspartic acid | 73 | 139 | 69 |
| Cysteine | | 4 | |
| Glutamic acid | 133 | 274 | 369 |
| Glycine | 4 | 1 | <0.5 |
| Proline | 322 | 6 | |
| Tryptophan | 350 | 55 | |

*Trace amounts of glycine and alanine are often found in hydrolyzates of thermal proteins even though they were not included in the reaction mixture.

TABLE 2

| EFFECT OF POLYMERS ON RETENTION OF FOOTSHOCK AVOIDANCE ONE WEEK AFTER ICV ADMINISTRATION | | | | | |
|---|---|---|---|---|---|
| | Dose of Thermal Protein (μg/brain, ICV) | | | | |
| | 0 | 1.13 | 2.25 | 4.5 | 9.0 |
| RS-III-54 | | | | | |
| Mean Trials to | 5.40 | 4.00 | 3.87 | 2.80 | 2.80 |
| 1st Avoidance (±SEM) | 0.36 | 0.35 | 0.44 | 0.41 | 0.21 |
| $p <$ * | | 0.05 | 0.05 | 0.01 | 0.01 |
| Mean Trials to | 9.60 | 8.07 | 8.07 | 6.80 | 7.13 |
| Criterion (±SEM) | 0.36 | 0.37 | 0.46 | 0.41 | 0.26 |
| $p <$ * | | 0.05 | 0.05 | 0.01 | 0.01 |
| GV-II-100UN | | | | | |
| Mean Trials to | 4.93 | | 4.47 | 3.60 | 2.87 |
| 1st Avoidance (±SEM) | 0.46 | | 0.44 | 0.38 | 0.33 |
| $p <$ * | | | | 0.05 | 0.01 |
| Mean Trials to | 9.07 | | 8.67 | 7.87 | 7.07 |
| Criterion (±SEM) | 0.49 | | 0.48 | 0.38 | 0.33 |
| $p <$ * | | | | | 0.01 |
| RS-IV-132DD | | | | | |
| Mean Trials to | 5.13 | | 5.27 | 4.73 | 5.00 |
| 1st Avoidance (±SEM) | 0.38 | | 0.48 | 0.43 | 0.32 |
| Mean Trials to | 9.27 | | 9.60 | 9.30 | 9.33 |
| Criterion (±SEM) | 0.38 | | 0.46 | 0.39 | 0.33 |

*The p values indicate significant mean differences between the 0 μg dose group and experimental groups as determined by Dunnett's t-test. The results of the one-way ANOVA's for trials to first avoidance were $F(3,56) = 5.53$, $p < 0.005$ for GV-II-100UN and $F(3,56) = 9.43$, $p < 0.001$ for RS-III-54. The results of the one-way ANOVA's for trials to criterion were $F(3,56) = 4.69$, $p < 0.01$ for GV-II-100UN and $F(3,56) = 9.04$, $p < 0.001$ for RS-III-54. RS-IV-132DD did not have a significant effect by either measure of retention (F's < 1).

Conclusion

Since the thermal proteins were administered after training and one week prior to testing retention, they could not have affected learning or directly affected retention test performance. Therefore, we interpret the reduction of the mean trials to first avoidance or to criterion resulting from the administration of GV-II-100UN and RS-III-54 as due to improved memory processing.

The utility of thermal proteins as pharmacologic agents is dependent upon being able to reproduce them reliably. In this regard, thermal proteins have been rigorously shown to be self-sequencing in a reproducible fashion (Fox and Windsor, 1984; Tyagi and Ponnamperuma, 1990).

Central administration of aspartic acid or glutamic acid can improve memory retention on the test reported in this study (Flood et al, 1990). However, in these thermal proteins low or high amounts of these acids is not related to the ability of the thermal protein to improve retention. Thermal protein RS-IV-132DD is high in glutamic acid but did not improve retention. Thermal protein RS-III-54, containing high proportions of both aspartic and glutamic acid, improved retention, but thermal protein GV-II-100UN, containing low porportions of these amino acids, also improved retention.

Proline can cause amnesia for both passive and active avoidance training administered centrally to chicks and mice (Davis and Cherkin, 1987). GV-II-100UN is high in proline; yet this polymer improved retention. Hefti et at (1991) found that the addition of free amino acids in the same proportions found in the thermal proteins did not have neurotrophic effects on cultured forebrain neurons. Thus, it seems likely that the polymers per se, rather than the individual amino acids themselves, affected memory processing.

The ability of the polymers to elicit electrical activity in cultured cells does not seem to be related to their ability to improve retention since RS-IV-132DD, which stimulated electrical activity (Vaughan et al, 1987), did not improve retention.

While the mechanism of action by which thermal proteins exert neurotrophic or memory improving effects is not known, hydrophobicity may be a contributing factor in improving retention as GV-II-100UN and RS-IV-54 are hydrophobic and improved retention, while RS-IV-132DD is not hydrophobic and did not improve retention. Hydrophobicity is also associated with neurotrophic effects on cultured neurons (Hefti et al, 1991). Proline in a polymer reduces its effects on neuronal sprouting while tryptophan stimulates it (Fox et al, 1987; Hefti et al, 1991). Hefti et al (1991) hypothesized that thermal proteins act on cell surfaces and may promote cell recognition which could be important in altering the pattern of synaptic connections thought to be the fundamental aspect of long term memory storage.

REFERENCES

U.S. Pat. No. 3,052,655, S. W. Fox and K. Harada, Thermal Polymerization of Amino Acid Mixtures Containing Aspartic Acid or a Thermal Precursor of Aspartic Acid (1962).

U.S. Pat. No. 3,076,790, S. W. Fox and K. Harada, Method of Making Copolymers of Amino Acids Containing Glutamic Acid (1963).

U.S. Pat. No. 4,315,072, S. W. Fox and A. I. Holden, Artificial Gelatins of High Methionine Content for Photographic Film (1982).

U.S. Pat. No. 4,534,881, C. S. Sikes and A. P. Wheeler, Inhibition of Inorganic or Biological $CaCO_3$ Deposition by Poly Amino Acid Derivatives (1985).

U.S. Pat. No. 4,514,584, S. W. Fox and A. T. Przybylski, Organic Photovoltaic Device (1985).

U.S. Pat. No. 4,925,673, S. Steiner and R. Rosen, Delivery Systems for Pharmacological Agents Encapsulated with Proteinoids (1990).

U.S. Pat. No. 4,963,364, S. W. Fox and R. W. Veltri, Microencapsulated Antitumor Agent (1990).

U.S. Pat. No. 4,976,968, S. Steiner, Anhydrous Delivery Systems for Pharmacological Agents (1990).

U.S. Pat. No. 4,996,292, S. W. Fox and P. R. Bahn, Self-Sealing Artificial Skin Comprising Copoly-Alpha-Amino Acid (1991).

J. L. Davis and A. Cherkin, Intraventricular L-Proline Induces Retrograde Amnesia in Chicks, IRCS Medical Press, Vol. 5, p. 88 (1987).

J. F. Flood, G. E. Smith, and A. Cherkin, Hydergine Enhances Memory in Mice, Journal of Pharmacology (Paris), Vol. 16, suppl. III, pp. 39–49 (1985).

J. F. Flood and A. Cherkin, Fluoxetine Enhances Memory Processing in Mice, Psychopharmacology, Vol. 93, pp. 36–43 (1987).

J. F. Flood, M. L. Baker, and J. L. Davis, Modulation of Memory Processing by Glutamic Acid Agonists and Antagonists, Brain Research, Vol. 521, pp. 197–202 (1990).

S. W. Fox, Synthesis of Life in the Lab? Defining a Protoliving System, Quarterly Review of Biology, Vol. 66, pp. 181–185 (1991).

S. W. Fox and K. Harada, Thermal Polycondensation of α-Amino Acids. In P. Alexander (ed.), A Laboratory Manual of Methods in Protein Chemistry. Vol. IV, Oxford: Pergamon Press, pp. 129–151 (1966).

S. W. Fox, J. Hafti, E. Hartikka, E. Junard, A. T. Przybylski, and G. Vaughan, Pharmacological Activities in Thermal Proteins: Relationships in Molecular Evolution, International Journal of Quantum Chemistry, Quantum Biology Symposium, Vol. 14, pp. 347–349 (1987).

S. W. Fox and T. V. Waehneldt, The Thermal Synthesis of Neutral and Basic Proteinoids, Biochemica Biophysica Acta, Vol. 160, pp. 246–249 (1986).

S. W. Fox and C. W. Windsor, Reproducibility of Amino Acid Compositions in Repeated Copolymerizations of Amino Acids, International Journal of Quantum Chemistry, Quantum Biology Symposium, Vol. 11, pp. 103–108 (1984).

D. O. Hebb. The Organization of Behavior. New York, John Wiley and Sons (1949).

F. Hefti, E. O. Junard, B. Knuesel, W. L. Strauss, P. F. Strang, A. Przybylski, G. Vaughan, and S. W. Fox, Promotion of Neuronal Survival In Vitro by Thermal Proteins and Poly (Dicarboxylic) Amino Acids, Brain Research, Vol. 541, pp. 273–283 (1991).

G. Keppel. Design and Analysis, A Researcher's Handbook. Englewood Cliffs, N.J., pp. 556–559 (1973).

S. Tyagi and C. Ponnanperuma, Nonrandomness in Prebiotic Peptide Synthesis, Journal of Molecular Evolution, Vol. 30, pp. 391–399 (1990).

G. Vaughan, A. T. Przybylski, and S. W. Fox, Thermal Proteinoids as Excitability-Inducing Materials, BioSystems, Vol. 20, pp. 219–233 (1987).

What is claimed is:

1. A memory enhancing protein produced by thermally polymerizing a mixture of α-amino acids consisting of aspartic acid, glutamic acid, proline, and tryptophan in the molar ratio of 1:1:3:3 respectively by heating the said amino acids for 5½ hours at 175°–180° C.

2. A memory enhancing protein produced by thermally polymerizing a mixture of α-amino acids consisting of aspartic acid, glutamic acid, tryptophan, and cysteine in the molar ratio of 1:3:1:1 respectively by heating the said amino acids for 5½ hours at 175°–180° C.

* * * * *